(12) United States Patent
Biedermann et al.

(10) Patent No.: US 7,771,458 B2
(45) Date of Patent: Aug. 10, 2010

(54) BONE FIXING DEVICE (75) Inventors: Lutz Biedermann, Villingen (DE); Jürgen Harms, Karlsruhe (DE); Alan Crockard, London (GB)

(73) Assignee: Biedermann Motech GmbH, VS-Schwenningen (DE)

( * ) Notice: Subject to any disclaimer, the term of this patent is extended or adjusted under 35 U.S.C. 154(b) by 782 days.

(21) Appl. No.: 10/279,196

(22) Filed: Oct. 23, 2002

(65) Prior Publication Data

US 2003/0078583 A1 Apr. 24, 2003

(30) Foreign Application Priority Data

Oct. 23, 2001 (DE) ................. 101 52 094

(51) Int. Cl.
*A61B 17/80* (2006.01)
(52) U.S. Cl. .................................... 606/289
(58) Field of Classification Search ............ 606/61, 606/69–73
See application file for complete search history.

(56) References Cited

U.S. PATENT DOCUMENTS

| 5,127,914 | A | * | 7/1992 | Calderale et al. .............. 606/65 |
| 5,261,910 | A | * | 11/1993 | Warden et al. ................. 606/61 |
| 5,578,034 | A | * | 11/1996 | Estes ............................ 606/61 |
| 5,607,426 | A | * | 3/1997 | Ralph et al. .................... 606/61 |
| 5,735,853 | A | | 4/1998 | Olerud |
| 6,017,345 | A | | 1/2000 | Richelsoph |
| 6,193,721 | B1 | * | 2/2001 | Michelson .................... 606/70 |
| 6,235,033 | B1 | * | 5/2001 | Brace et al. ................... 606/69 |
| 6,290,703 | B1 | * | 9/2001 | Ganem ......................... 606/73 |
| 6,533,786 | B1 | * | 3/2003 | Needham et al. .............. 606/61 |
| 6,641,583 | B2 | * | 11/2003 | Shluzas et al. ................ 606/61 |
| 6,652,525 | B1 | | 11/2003 | Assaker et al. |
| 6,692,503 | B2 | * | 2/2004 | Foley et al. ................... 606/96 |
| 7,004,944 | B2 | * | 2/2006 | Gause .......................... 606/69 |

FOREIGN PATENT DOCUMENTS

| CH | 672 245 | | 11/1989 |
| EP | 0 897 697 A1 | | 2/1999 |
| EP | 0 903 113 | | 3/1999 |
| EP | 0 903 113 A2 | | 3/1999 |
| FR | 2 726 461 | | 5/1996 |
| FR | 2 778 088 | | 11/1999 |
| WO | WO96/05778 | | 2/1996 |
| WO | WO 96/05778 | | 2/1996 |
| WO | WO9851226 | * | 11/1998 |
| WO | WO 00/18312 | | 4/2000 |
| WO | WO 01/26566 A1 | | 4/2001 |

* cited by examiner

*Primary Examiner*—Anu Ramana
(74) *Attorney, Agent, or Firm*—Christie, Parker & Hale LLP (57) ABSTRACT

A bone fixing device and in particular a device for stabilizing cervical vertebrae is provided, (with) a plate (2, 200) with at least one recess (5) for guiding through a section (15, 61, 62) of a bone screw (6, 60), a connecting element (20, 30), displaceable in the recess, for connecting the bone screw to the plate and a securing device (10, 11) for securing the connecting element against falling out of the recess.

22 Claims, 6 Drawing Sheets

BONE FIXING DEVICE

BACKGROUND OF THE INVENTION

The invention relates to a bone fixing device and in a particular application to a device for stabilising cervical vertebrae.

A device especially for stabilising cervical vertebrae is known, comprising a plate with at least one bore, having an M-thread, and a bone screw for screwing into the plate. The bone screw has a thread section, having a bone thread, for screwing into the bone and an adjoining thread section with an outer M-thread. In operation the bone screw is guided through the bore and screwed into the bone. Then the second thread section is screwed into the plate. Because the thread pitches are different there is a danger that the bone screw will thereby be loosened from its seat.

From WO 96/05778 a cervical vertebrae stabilising system is known which has a plate with at least one recess, a bone screw with a bone thread section and an adjoining M-thread section and a radial projection provided between the bone thread section and the M-thread section, and also a nut cooperating with the M-thread section. With this known device first the bone screw is screwed into the bone, then the plate with the recess is guided over the M-thread section until it rests against the radial projection and then the nut is inserted into the recess and screwed on to the M-thread section to fix it. The recess can be constructed as an elongated hole.

From WO 00/18312 a stabilising device for the spinal column is known, which has a plate with at least one recess, a bone screw with a bone thread section and an M-thread section and a projection provided between these sections and with a plain washer located on top of the edge of the recess, and also a nut which is screwed on over the M-thread section of the bone screw until it is adjacent to the shim. The plain washer has a lateral recess, so the bone screw can take up various angles.

The known systems are suitable for particular applications in each case. With the first mentioned device, for instance, the plate must always be put in first and then the screw screwed in. With the device known from WO 96/05778, on the other hand, the screw has to be screwed in first and then the plate placed on top. Additionally, with this device it is not possible to change the angle of the screw. The device known from WO 00/18312 admittedly allows different angles of the bone screw, but adjustment of the plate in the longitudinal direction is possible only to a limited extent. Additionally, this device has a relatively high construction.

SUMMARY OF THE INVENTION

The object of the invention is to provide a bone fixing device and in particular a device for stabilising cervical vertebrae, which is improved with respect to adjustability and breadth of application compared with the known devices.

This object is achieved by a bone fixing device according to patent claim 1. Further developments of the invention are cited in the dependent claims.

The invention has the particular advantage of a modular system, which considerably enlarges the breadth of application. The apparatus according to the invention is not only usable for cervical vertebrae stabilisation, but also as a bone fixing device for fixing broken bones, e.g. tubular bones. The invention further enables the surgeon in the operating room to make a decision, adapted to the circumstances of the individual case, as to whether the screws should be inserted first and then the plate placed over them and fixed or whether the plate should be put in first and then the bone screws screwed in through the recesses of the plate. The invention further allows monoaxial and polyaxial screws to be used together with one plate or even both types of screws next to one another. In this way adjustment of the angle of the screws to the plate and positioning of the screws for adjusting their longitudinal distance is possible independently for each screw.

Further features and advantages of the invention emerge from the description of embodiment examples with the aid of the figures.

DETAILED DESCRIPTION OF THE DRAWINGS

As can be seen from FIGS. 1 to 4, the bone fixing device 1 has a substantially rectangular plate 2 with rounded corners. For further description the midline of the plate running in the longitudinal direction of the rectangle is designated as D and the midline running perpendicularly to it in the crosswise direction as C. The plate has a first end 3 and a second end 4 opposite this with recesses 5, provided in each case near the ends, for receiving bone screws. Each recess 5 has a first area 5a with a first diameter $d_1$ in a direction perpendicular to midline D and a second area 5b with a second diameter $d_2$ in a direction perpendicular to midline D, wherein the second diameter $d_2$ is larger than the first diameter $d_1$. The total diameter of the recess 5 in the longitudinal direction, in other words on midline D, is larger than the second diameter $d_2$. Areas 5a and 5b are formed, for example, by an elongated hole, the small diameter of which corresponds to the diameter of area 5a, and an additional bore with the larger diameter $d_2$ of area 5b. Areas 5a and 5b are arranged on the plate in such a way that area 5b is facing away from the respective end 3 or 4 of the plate and points towards midline C. On the upper side 2a of the plate 2 facing away from the shank of the bone screw 6 in a state of use each recess 5 has an indentation 7 for receiving a subsequently described connecting element.

The plate 2 further has, bordering on areas 5b of the recesses 5, thread bores 8, located opposite one another, with an indentation 9 for screwing in screws 10 with a head 11, which are constructed, for example, as slit screws. The thread bore 8 is provided at such a distance from area 5b of the recess 5, and the indentation 9 and the head 11 of the screw 10 are dimensioned in such a way, that in the screwed in state the head 11 projects just a little into the area of the indentation 7 in area 5b of the recess 5 and thus limits the cross-section of the indentation 7.

Figure 1:
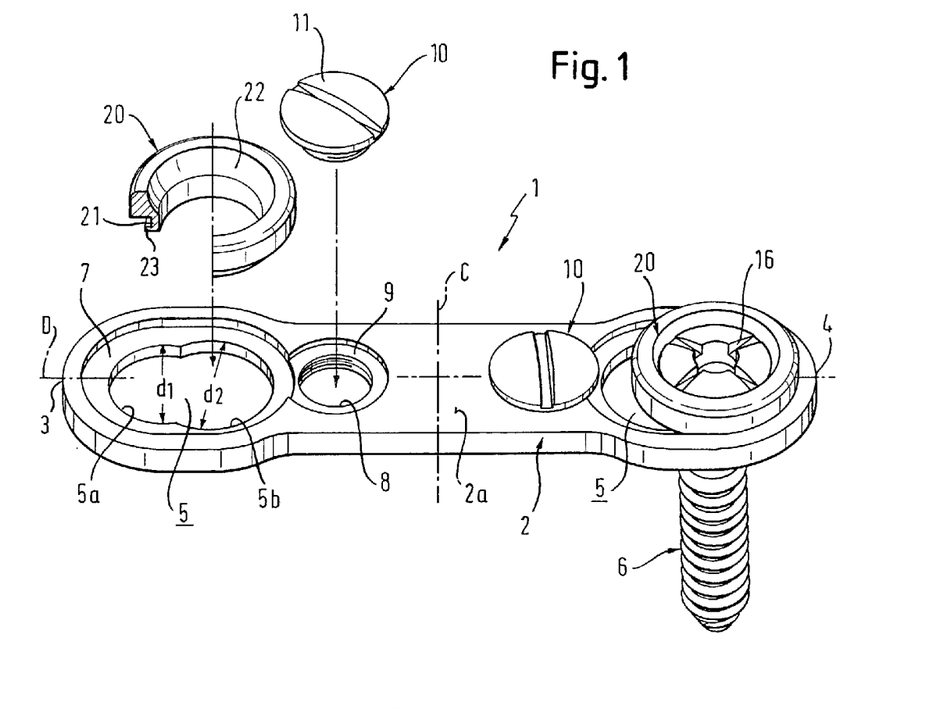
FIG. 1 shows a perspective view of the bone fixing device according to a first embodiment.
Figure 2:
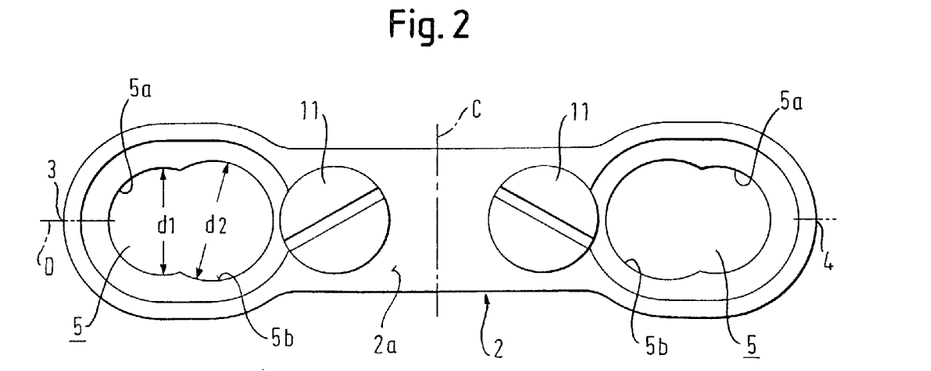
FIG. 2 shows a horizontal projection on to the plate of the bone fixing device according to FIG. 1.
Figure 3:
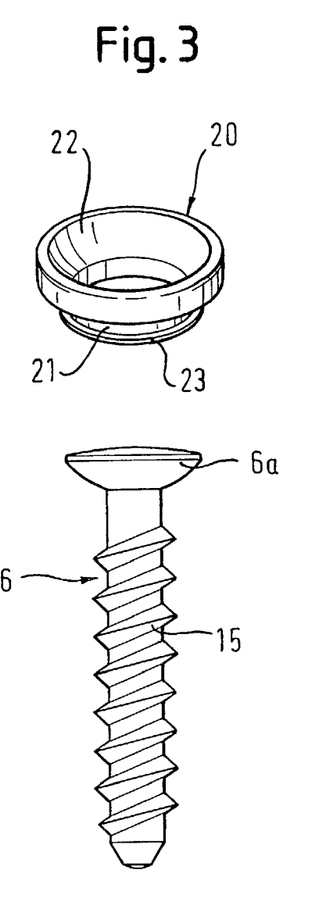
FIG. 3 shows a perspective exploded representation of the bone screw and the plain washer of the bone fixing device according to FIG. 1.
Figure 4:
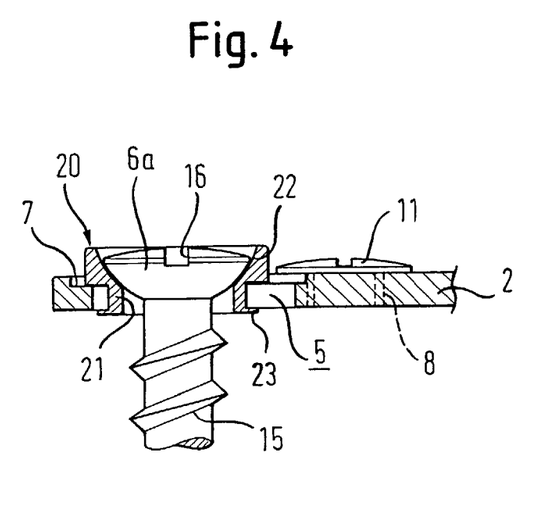
FIG. 4 shows a section through a part of the bone fixing device according to FIG. 1.

As can be seen in particular from FIGS. 1, 3 and 4, for connecting the bone screw to the plate 2 the bone fixing device has a connecting element in the form of a supporting element or shaped part, constructed as sleeve-shaped, called hereinafter a plain washer 20. The plain washer 20 has a hollow cylindrical section 21, the length of which is slightly greater than the thickness of the plate in the area of the recess 5. On the side arranged in the state inserted into the plate 2 on the upper side 2a of the plate the plain washer 20 is constructed with a section 22, shaped as a hollow spherical segment, the outer diameter of which is smaller than the diameter of the indentation 7 crosswise to midline D, but greater than the diameter $d_2$ of the second area 5b, so in the inserted state the plain washer 20 with the area 22 lies on top at the edge of the indentation 7. Section 22, shaped as a hollow spherical segment, is constructed on the inside with a spherical radius corresponding to the spherical radius of a head 6a of the bone screw 6 shaped as a spherical segment. At the end facing away from the section 22, shaped as a hollow spherical segment, the plain washer 20 has a ring-shaped projection 23, the outer diameter of which is larger than the diameter $d_1$ of the first area 5a of the recess 5 and smaller than the diameter $d_2$ of the second area 5b of the recess 5. The plain washer 20 is thus so dimensioned that it can be inserted through area 5b with the larger diameter $d_2$ of the recess 5 into the recess 5 and can be displaced in the longitudinal direction of the plate in the indentation 7 until it is in area 5a, from which it cannot fall out. The indentation 7 forms a guide for the plain washer.

The bone fixing device 1 of the first embodiment further has the bone screw 6, which in this embodiment is constructed in one piece, with a shank 15 with a bone thread for screwing into the bone and with the head 6a, which is shaped as a spherical segment and firmly connected to the shank and on its upper side has a means 16, e.g. one of more slits, for bringing into engagement with a screwing-in tool.

In operation first the plain washer 20 is guided in through area 5b of the recess 5, so the section 22, shaped as a hollow spherical segment, is located on the upper side 2a of the plate. Then the plain washer is pushed in the direction of area 5a, wherein the underside of section 22, shaped as a hollow spherical segment, is lying on top in the indentation 7. In area 5a with the smaller diameter $d_1$ the plain washer 20 is held against falling out owing to the larger diameter of section 22, shaped as a hollow spherical segment, and the projection 23. Then the securing screw 9 is screwed into the bore 8. The edge of the head 11 of the securing screw 9 therein projects, as can be seen in particular from FIGS. 1, 2 and 4, slightly into the area of the indentation 7 of the recess 5 and thus limits the diameter of the indentation 7 in area 5b, securing the plain washer 20 from falling out after it has been inserted. However, the plain washer 20 is still therein displaceable in the longitudinal direction in the recess 5 and is pushed to the exact position desired. Then the bone screws 6 with the thread shank 15 with the bone thread are guided through the plain washer and screwed into the bone.

During an operation the surgeon uses the plate with already inserted plain washers 20, secured against falling out by the screws 10, which thus in each case form an integrated shaped part, and holds them against the bone parts to be fixed and then screws in the bone screws 6. Since the plain washer can be displaced, adjustment of the screwing position is possible before screwing down.

Figure 5:
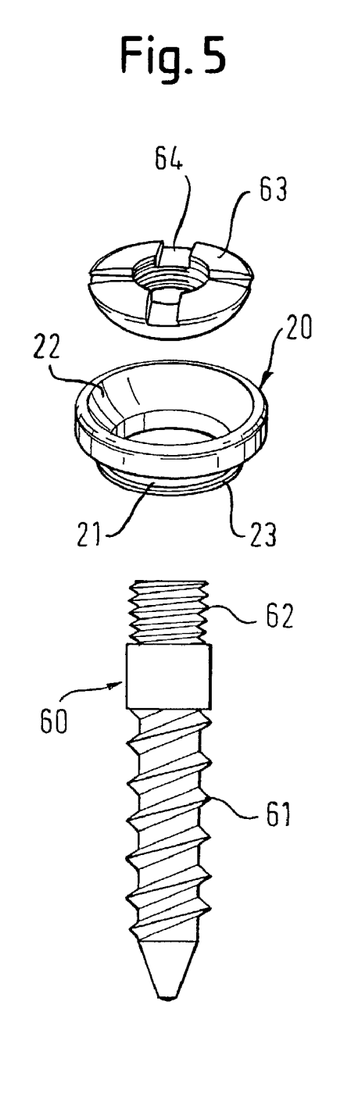
FIG. 5 shows a perspective exploded representation of a bone fixing device according to a second embodiment.
Figure 6:
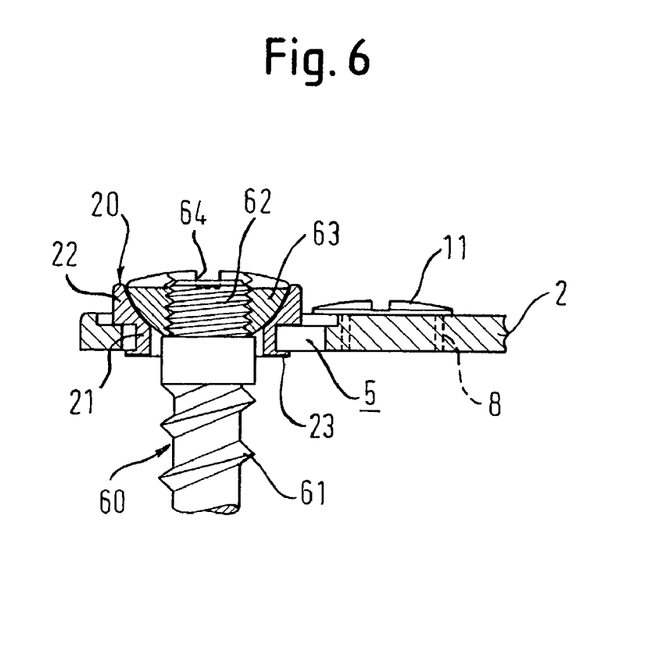
FIG. 6 shows a section through the bone fixing device according to the second embodiment.

The embodiment shown in FIGS. 5 and 6 is, as far as the plate 2 is concerned, identical to the embodiment shown in FIGS. 1 to 4. However, in this embodiment the bone screw 60 is different. Bone screw 60 has a first thread shank section 61 with a bone thread and an adjoining second thread shank section 62 with an M-thread. The diameter of the second thread section 62 is smaller than the inner diameter of the plain washer 20, so the second thread section 62 can be guided through the plain washer 20 constructed like a sleeve. At its end opposite the tip of the bone screw the bone screw has a hexagonal recess, not shown, for bringing into engagement with a screwing-in tool for screwing the bone screw into the bone.

In this embodiment the head of the screw 60 is formed by a separate nut 63, which is shaped in the form of a spherical segment with a radius corresponding to that of section 22, shaped as a hollow spherical segment, of the plain washer 20. The nut 63 has on its upper side facing away from the part shaped as a spherical segment a means 64, such as e.g. slits, for bringing into engagement with a screwing-in tool.

In operation again first the plain washer or the plain washers 20 is/are guided into the recesses 5 of the plate 2 and secured against falling out via the screw 10. During the operation first the plate 2 is held against the bone parts to be fixed and the screwing in position for the bone screws marked. Then the bone screws 60 are screwed in and the plate 2 with the recesses 5 placed over the second thread section 62 projecting from the bone. Then the nut 63 is screwed on to the second thread section until it comes to rest in section 22, shaped as a hollow spherical segment, of the plain washer 20, wherein, owing to the spherical sections of the plain washer 20 and the nut 63, angles of the bone screw are possible in a predetermined range of angles.

Figure 7:
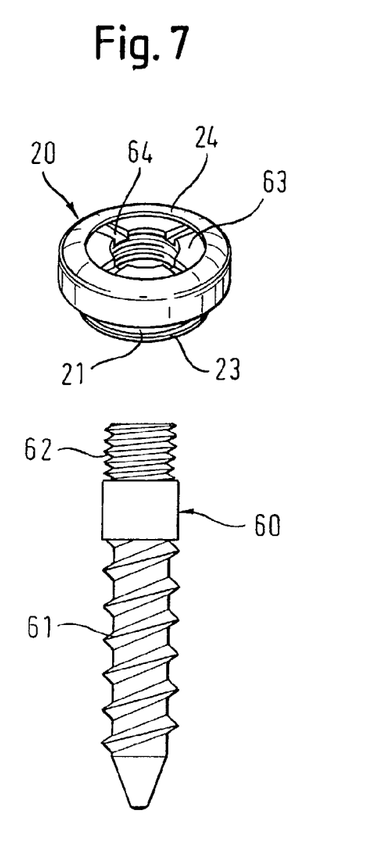
FIG. 7 shows a perspective exploded representation of a bone fixing device according to a third embodiment.
Figure 8:
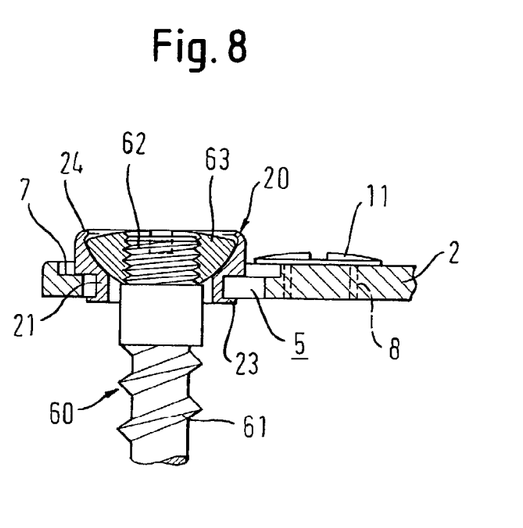
FIG. 8 shows a section through the bone fixing device of the third embodiment.

The embodiment shown in FIGS. 7 and 8 differs from the embodiments shown in FIGS. 5 and 6 in that on the outer end of section 22, shaped as a hollow spherical segment, the plain washer 20 has an edge 24, projecting inwards by a predetermined measurement, encircling the inserted nut 63, starting from its upper side, by a predetermined measurement, so the nut 63 is secured against falling out.

In operation with this embodiment the plain washer 20 is pre-fabricated with the nut 63 already inserted and, as with the previously described embodiments, is first inserted into the plate 2 and secured against falling out with the securing screw 10. Further operation is as with the embodiment shown in FIGS. 5 and 6. This embodiment has the advantage that the nut 63 is held and thus cannot be dropped by the surgeon during the operation.

Figure 9:
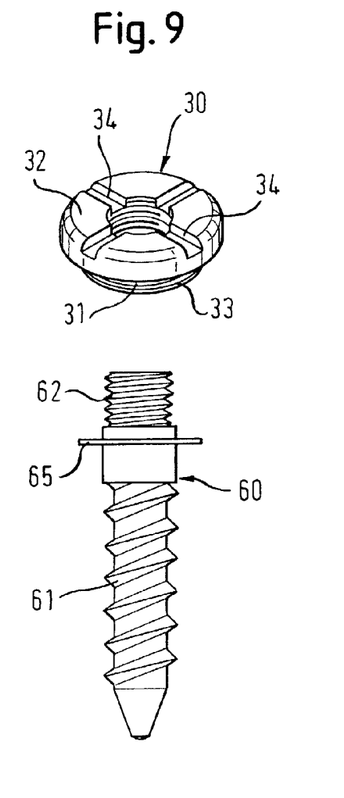
FIG. 9 shows a perspective exploded representation of a bone fixing device according to a fourth embodiment.
Figure 10:
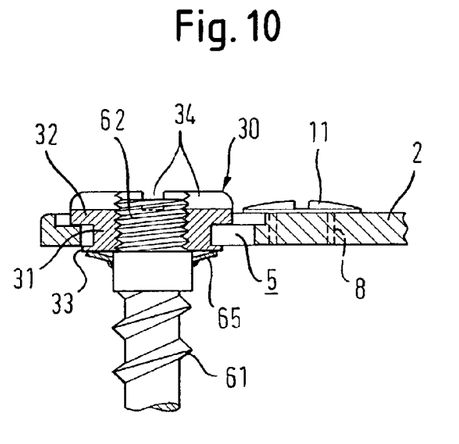
FIG. 10 shows a section through the bone fixing device according to the fourth embodiment.

In the embodiment shown in FIGS. 9 and 10 the connecting element between the plate and the bone screw is constructed as a nut 30, instead of as a plain washer, for screwing on to the second thread shank section 62 of the bone screw 60. The nut 30 has a first area 31, corresponding in its dimensions to the hollow-cylindrical central part 21 of the plain washer of the previous embodiments, but has an inner thread. Bordering on one end of this central section the nut 30 has a head section 32 with an outer diameter, which, as with the plain washer 20, is slightly smaller than the diameter of the indentation 7 but larger than the diameter $d_2$ of the second area 5b of the recess 5. Bordering on the other end of the central area 31, as with the plain washer, a ring-shaped projection 33 is provided. The nut 30 additionally also has on its upper side means 34, such as e.g. slits, for engaging with a screwing-in tool.

In this embodiment the bone screw 60 is provided with a shoulder 65, arranged between the bone thread shank section 61 and the thread shank cutout 62 with the M-thread, which shoulder is formed, for example, as a ring-shaped projection and serves as a stop during screwing in, as illustrated in particular in FIG. 10.

In operation the bone screw or bone screws 60 is/are screwed in at the previously determined positions and then the plate with the recesses 5 is placed over the thread sections 62 and then the nut 30 screwed on.

Figure 11:
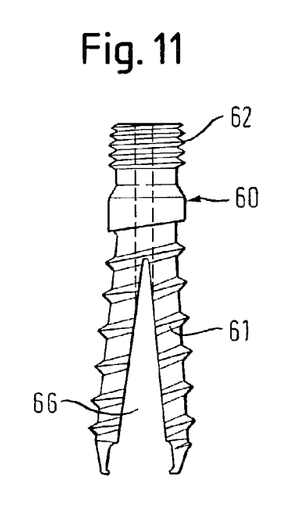
FIG. 11 shows a perspective representation of a modification of the bone screw of the preceding embodiments.

In the embodiment shown in FIG. 11 the bone screw of the bone thread shank section is constructed as hollow and provided with two opposite longitudinal slits 66. Further provided is an expanding element, not illustrated in the figure, on the inside of the shank, which can be actuated in such a way that the shank sections formed by the longitudinal slits 66 can be expanded apart. After the bone thread shank section has been screwed in an expanding effect is thus achieved, which guarantees an improved hold.

Figure 12:
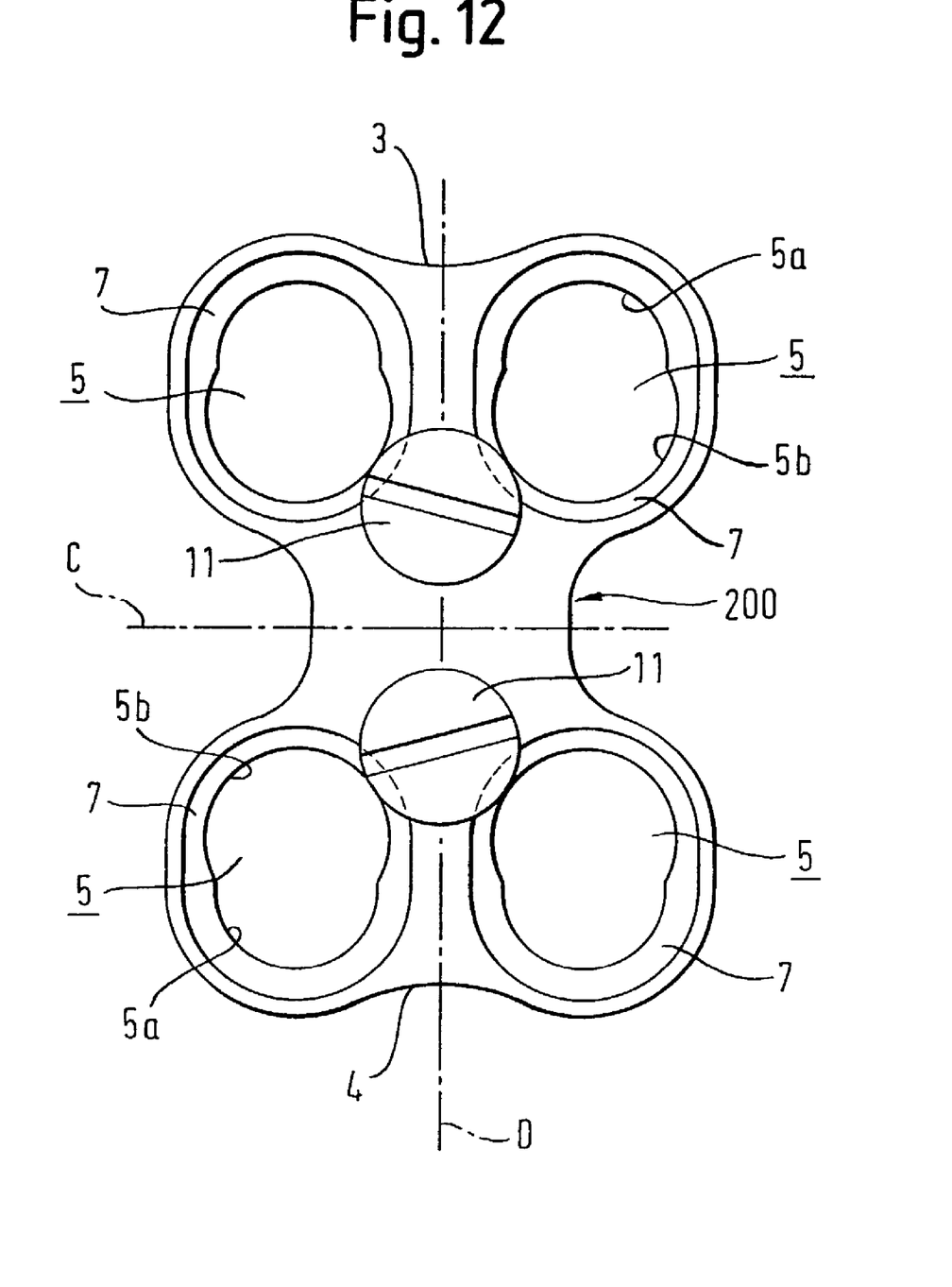
FIG. 12 shows a modified form of the plate of the bone fixing device of the preceding embodiments.

In the embodiment illustrated in FIG. 12 the plate 200 is constructed in particular for application in cervical vertebrae stabilisation and has on each end 3, 4 in each case two recesses 5, wherein in each case two adjacent recesses 5 share a securing screw 10. For this purpose the axis of the bore 8 for the securing screw 10 is arranged on the central longitudinal axis D and the dimension of the screw head 11 and the position of the bore are chosen in such a way that in the screwed in state the screw head 11 engages in both indentations 7 of the adjacent recesses 5. The plate 200 is further constructed as waisted.

The embodiments described can be combined on a plate in any way or the screws, depending on the purpose, can be used for the various embodiments, guaranteeing a modular system with great versatility.

Instead of the securing screw 10, a different securing element can be provided, for example a spring element attached to the plate, which is bent away for inserting the plain washer 20 or the nut 30 and then snaps back to limit the cross-section of the recess.

The term plate is to be understood also to include elements with a not completely flat, for example a bent or in some other way curved, surface.

The device according to the invention can be not only applied to stabilising cervical vertebrae, but is also suitable for the external fixing of broken bones, e.g. tubular bones.

What is claimed is:

1. A fixing device for bones, said device comprising:
   a plate extending in a longitudinal direction, the plate having a first outwardly facing surface and a second outwardly facing surface opposite from the first outwardly facing surface, the plate defining at least one recess through the plate in a direction transverse to the longitudinal direction and through the first and second outwardly facing surfaces;
   a bone screw configured to be screwed into a bone, the bone screw having a tip and an opposite end facing away from the tip, the tip being structured and arranged to pass through the recess;
   a connecting element comprising a sleeve-shaped element defining a central opening along a central axis extending from a first end of the connecting element to a second end of the connecting element, the connecting element located in the recess of the plate with the second end of the connecting element extending past the second outwardly facing surface of the plate in a direction away from the first outwardly facing surface of the plate; and
   a securing device for securing the connecting element in the recess;
   wherein the recess comprises an elongated hole extending in the longitudinal direction, the elongated hole having a first area a contiguous second area;
   wherein an outer diameter of the second end of the connecting element is smaller than a second diameter of the second area to pass completely through the recess when moved through the second area of the recess in a direction perpendicular to the longitudinal direction and the outer diameter of the second end of the connecting element is larger than a first diameter of the first area to prevent the second end of the connecting element from passing completely through the recess when moved through the first area of the recess in the direction perpendicular to the longitudinal direction;
   wherein the bone screw is located within the central opening of the sleeve-shaped element of the connecting element.

2. The fixing device according to claim 1, wherein the second end of the sleeve-shaped element has a projection generally perpendicular to the central axis, the projection having an outer diameter that is larger than an inner diameter of the first area of the recess and that is smaller than an inner diameter of the second area and wherein the sleeve-shaped element has an outer diameter at the first end that is larger than the inner diameter of the second area.

3. The fixing device according to claim 1, wherein the plate has a thickness between the first and second outwardly facing surfaces, and the sleeve-shaped element has a length from the first end to the second end that is larger than the thickness of the plate in the area of the recess.

4. A fixing device for bones, said device comprising:
   a plate having at least one recess;
   a bone screw configured to be screwed into a bone, the bone screw having a tip and an opposite end facing away from the tip, the tip being structured and arranged to pass through the recess;
   a connecting element for connecting the bone screw with the plate; and
   a securing device for securing the connecting element in the recess;
   wherein the recess comprises a first area in which the connecting element is held, and in the plate surface adjoining the first area along a length of the plate, a second area having a larger diameter than the first area, so that the connecting element is inserted into the recess from the second area and is then laterally displaceable in the recess along the length of the plate toward the first area, and wherein the securing device is configured to secure the connecting element in the laterally displaced position; and,
   wherein the bone screw comprises a head and a shaft portion, the head of the bone screw comprising a nut removably attached to the shaft, the nut having a first spherical segment, and wherein the connecting element comprises a hollow second spherical segment for receiving the first spherical segment of the nut.

5. The fixing device according to claim 4, wherein the connecting element is structured and arranged so that, when the hollow second spherical segment encircles the first spherical segment of the first spherical segment of the nut, the nut is enclosed.

6. A fixing device for bones, said device comprising:
a plate having at least one recess;
a bone screw configured to be screwed into a bone, the bone screw having a tip and an opposite end facing away from the tip, the tip being structured and arranged to pass through the recess;
a connecting element for connecting the bone screw with the plate; and
a securing device for securing the connecting element in the recess;
wherein the recess comprises a first area in which the connecting element is held, and in the plate surface adjoining the first area along a length of the plate, a second area having a larger diameter than the first area, so that the connecting element is inserted into the recess from the second area and is then laterally displaceable in the recess along the length of the plate toward the first area, and wherein the securing device is configured to secure the connecting element in the laterally displaced position;
wherein the connecting element comprises a sleeve-shaped element that is structured and arranged to receive the opposite end of the bone screw facing away from the tip; and
wherein the sleeve-shaped element has a first end and a second end, the first end having a projection, the projection having an outer diameter that is larger than a first diameter of the first area of the recess and that is smaller than a second diameter of the second area and wherein the sleeve-shaped element has a third outer diameter at the second end that is larger than the second diameter of the second area.

7. A fixing device for bones, said device comprising:
a plate having at least one recess;
a bone screw configured to be screwed into a bone, the bone screw having a tip and an opposite end facing away from the tip, the tip being structured and arranged to pass through the recess;
a connecting element for connecting the bone screw with the plate; and
a securing device for securing the connecting element in the recess;
wherein the recess comprises a first area in which the connecting element is held, and in the plate surface adjoining the first area along a length of the plate, a second area having a larger diameter than the first area, so that the connecting element is inserted into the recess from the second area and is then laterally displaceable in the recess along the length of the plate toward the first area, and wherein the securing device is configured to secure the connecting element in the laterally displaced position;
wherein the connecting element comprises a sleeve-shaped element that is structured and arranged to receive the opposite end of the bone screw facing away from the tip; and
wherein the plate has a thickness, the recess has an edge, and the sleeve-shaped element has a length from a first end to a second end that is slightly larger than the thickness of the plate in the area of the recess.

8. A fixing device for bones, said device comprising:
a plate having at least one recess;
a bone screw configured to be screwed into a bone, the bone screw having a tip and an opposite end facing away from the tip, the tip being structured and arranged to pass through the recess;
a connecting element for connecting the bone screw with the plate; and
a securing device for securing the connecting element in the recess;
wherein the recess comprises a first area in which the connecting element is held, and in the plate surface adjoining the first area along a length of the plate, a second area having a larger diameter than the first area, so that the connecting element is inserted into the recess from the second area and is then laterally displaceable in the recess along the length of the plate toward the first area, and wherein the securing device is configured to secure the connecting element in the laterally displaced position;
wherein the securing device comprises a securing element limiting the cross-section of the second area; and
wherein the securing device comprises a screw having a head with a fourth diameter, the screw being structured and arranged such that, when fixedly positioned in the plate, the fourth diameter of the head projects into the second area of the recess to such an extent that it prevents the connecting element from removal.

9. A fixing device for bones, said device comprising:
a plate having a length along a longitudinal axis of the plate and at least one recess passing completely through a thickness of the plate;
a bone screw configured to be screwed into a bone, the bone screw having a tip and an opposite end facing away from the tip, the tip being structured and arranged to pass through the recess;
a connecting element for connecting the bone screw with the plate, the connecting element comprising a sleeve-shaped element defining a central opening, wherein the bone screw is located within the central opening of the sleeve-shaped element of the connecting element; and
a securing device for securing the connecting element in the recess;
wherein the recess is elongated in a direction along the longitudinal axis of the plate and comprises a first area in which the connecting element is held, and adjoining the first area along the length of the plate a contiguous second area having a larger diameter than the first area, so that the connecting element is inserted into the second area of the recess and is then displaceable in the recess along the longitudinal axis of the plate into the first area; and
wherein the securing device is configured to limit movement of the connecting element in the second area.

10. The fixing device according to claim 9, wherein the plate further defines a bore spaced from the recess to receive the securing device, the securing device comprising a securing element that projects along the longitudinal axis to limit passage of the connecting element fully into the second area when moved along the longitudinal axis.

11. The fixing device according to claim 10, wherein the securing device comprises a screw having a head with an outer diameter, the screw being structured and arranged such that, when fixedly positioned in the plate, the outer diameter of the head projects along the longitudinal axis to limit passage of the connecting element fully into the second area when moved along the longitudinal direction.

12. The fixing device according to claim 9, wherein the sleeve-shaped element is structured and arranged to receive the opposite end of the bone screw facing away from the tip.

13. The fixing device according to claim 9, wherein the opposite end of the bone screw comprises a head with a first spherical segment, and the connecting element comprises a hollow second spherical segment for receiving the first spherical segment of the head of the bone screw.

14. The fixing device according to claim 13, wherein the bone screw comprises a shaft section having a bone thread and the head is integral with the shaft section.

15. The fixing device according to claim 9, wherein the bone screw comprises a head and a shaft portion, and wherein the connecting element is removably attached to the head of the bone screw.

16. The fixing device according to claim 9, wherein the bone screw comprises a first shaft section having a bone thread and, adjacent thereto, a second shaft section having a thread for connecting to a nut.

17. The fixing device according to claim 16, wherein the bone screw further comprises a shoulder between the first shaft section and the second shaft section.

18. The fixing device according to claim 9, wherein the tip of the bone screw comprises a slit extending from the tip toward the opposite end.

19. The fixing device according to claim 9, wherein the recess further comprises an indentation.

20. The fixing device according to claim 9, wherein the plate has two recesses located adjacent to one another and the securing device is positioned to prevent removal of a the connecting element from both recesses.

21. The fixing device according to claim 9, wherein the bone screw comprises a head and a shaft portion, the head of the bone screw comprising a nut removably attached to the shaft, the nut having a first spherical segment, and wherein the connecting element comprises a hollow second spherical segment for receiving the first spherical segment of the nut.

22. The fixing device according to claim 21, wherein the connecting element is structured and arranged so that, when the hollow second spherical segment encircles the first spherical segment of the nut, the nut is enclosed.

* * * * *

UNITED STATES PATENT AND TRADEMARK OFFICE
CERTIFICATE OF CORRECTION

| | | |
|---|---|---|
| PATENT NO. | : 7,771,458 B2 | |
| APPLICATION NO. | : 10/279196 | |
| DATED | : August 10, 2010 | |
| INVENTOR(S) | : Lutz Biedermann et al. | |

It is certified that error appears in the above-identified patent and that said Letters Patent is hereby corrected as shown below:

In the Claims

Column 6, Claim 1, line 5          After "area" Insert -- and --

Column 6, Claim 5, line 62         Delete "of the first spherical segment"

Column 10, Claim 20, line 5        Delete "a"

Signed and Sealed this
Ninth Day of August, 2011

David J. Kappos
*Director of the United States Patent and Trademark Office*